(12) United States Patent
Wiberg et al.

(10) Patent No.: US 6,392,246 B1
(45) Date of Patent: May 21, 2002

(54) INTEGRATED RADIATION SHIELD

(75) Inventors: Peter Wiberg, Bälinge; Jan Olof Bergström, Uppsala, both of (SE)

(73) Assignee: Gems Pet Systems AB, Uppsala (SE)

( * ) Notice: Subject to any disclaimer, the term of this patent is extended or adjusted under 35 U.S.C. 154(b) by 0 days.

(21) Appl. No.: 09/787,947

(22) PCT Filed: Sep. 23, 1999

(86) PCT No.: PCT/SE99/01660

§ 371 Date: May 4, 2001

§ 102(e) Date: May 4, 2001

(87) PCT Pub. No.: WO00/19450

PCT Pub. Date: Apr. 6, 2000

(30) Foreign Application Priority Data

Sep. 29, 1998 (SE) ............................................. 9803300

(51) Int. Cl.[7] ................................................ G21F 5/00
(52) U.S. Cl. ................................... 250/506.1; 250/507.1
(58) Field of Search ........................... 250/506.1, 507.1

(56) References Cited

U.S. PATENT DOCUMENTS 4,020,351 A  4/1977  Gemmill, Sr. et al.
4,535,250 A * 8/1985  Fields ..................... 250/507.1
5,102,615 A * 4/1992  Grande et al. .............. 376/272

FOREIGN PATENT DOCUMENTS

| GB | 1228002 A | 4/1971 |
| NO | 167115 B | 6/1991 |
| SE | 437739 B | 3/1985 |

* cited by examiner

*Primary Examiner*—John R. Lee
*Assistant Examiner*—Sharon Payne

(57) ABSTRACT

An apparatus is disclosed that forms a basic integrated radiation shield for a PET isotope production system to create a safe environment. The apparatus and the system combine several subsystems to provide a high degree of integration and a nice aesthetic impression. The apparatus contains a cyclotron system and contains integrated target media handling for gas targets and water dispensing systems for water targets. A compartment including first and second additional radiation shields, respectively, that contains additional processing systems. The apparatus forms a closed radiation-proof system by means of a casing formed of four molded sections. A first and second section constitute a main body containing;the cyclotron system and a third and a fourth section constituting a pair of tight doors for encompassing the cyclotron into a sealed radiation shield. The first section additionally contains a Waste Gas Delay Line embedded in its shielding material.

10 Claims, 3 Drawing Sheets

INTEGRATED RADIATION SHIELD

This application is the national phase under 35 U.S.C. § 371 of PCT International Application No. PCT/SE99/01660 which has an International filing date of Sep. 23, 1999, which designated the United States of America and was published in English.

TECHNICAL FIELD

The present invention relates to isotope production and more specifically to a unique design of an Integrated Radiation Shield for a PET isotope production system.

BACKGROUND OF THE INVENTION

A PET (Positron Emission Tomography) isotope production system is complex with several subsystems and functions. Such a system produces radioactive tracers, which means that the system has to be in harmony with a number of regulations for such activities, particularly regarding radiation hazards. The customer (for instance a hospital working together with several contractors during set up and commissioning period) has to provide a facility fulfilling all requirements for the PET isotope production system such as necessary space with adequate floor load capacity (heavy equipment), mains power, primary cooling water, gas supply, ventilation, compressed air, drains, etc. The customer also has to set up the necessary laboratory capacity for the preparation of the radioactive tracers and to train the staff for the coming activities and so forth.

Consequently, setting up a new facility for production of PET isotope tracers is a multi-task undertaking which easily may lead to overspent budgets and loss of time for preparation and realisation of the project, which always will have an undesirable impact on such a project both for customers and vendors.

Consequently there is a need for a product with as few main components as possible, i.e. a high degree of system integration is a good contribution in making the planning of the facility easier. The customer then quickly gets a good overview of the delivered system and the number of interactions between the PET isotope production systems and the customer's own facility may be limited. Another bonus with such a philosophy is that the product installation will be almost identical from customer to customer making product documentation, upgrading, spare part handling and other after sales activities more effective, which will be beneficial for all parties.

SHORT DESCRIPTION OF THE INVENTION

The present invention presents an apparatus and a system forming a basic integrated radiation shield function for a PET isotope production cyclotron (referred to as the "MINItrace" device) to create a safe radiation environment. The apparatus and the system also combine several subsystems to present a design with a high degree of integration and a nice aesthetic impression.

The system according to the present invention is defined by the independent claim 1 and further embodiments are set forth by the dependent claims 2–5. Similarly, an apparatus incorporating the system is set forth by the independent claim 6, and different embodiments of the apparatus are defined by the dependent claims 7–10.

SHORT DESCRIPTION OF THE DRAWINGS

The objects, features and advantages of the present invention as mentioned above will become apparent from the description of the invention in conjunction with the following drawings, in which same or equal elements will be denoted by the same numerals, and wherein.

DESCRIPTION OF AN ILLUSTRATIVE EMBODIMENT

By means of FIGS. 1–6 an illustrative embodiment of the present invention will be described. This embodiment forms the "MINItrace" Integrated Radiation Shield:

A primary object of the invention is to create a radiation shield for a PET isotope production system, which presents a single unit having a limited size making it suited to be operated at an adequate floor size available for instance at a regular hospital utilising radioactive tracers in the form of short–lived isotopes.

Another object of the invention is to still achieve a design of the radiation shield, which also presents an aesthetic timeless design. Therefore the radiation shield and its integrated subsystems are housed in a carefully shaped shell, which is still offering the full desirable radiation protection shield.

Figure 1:
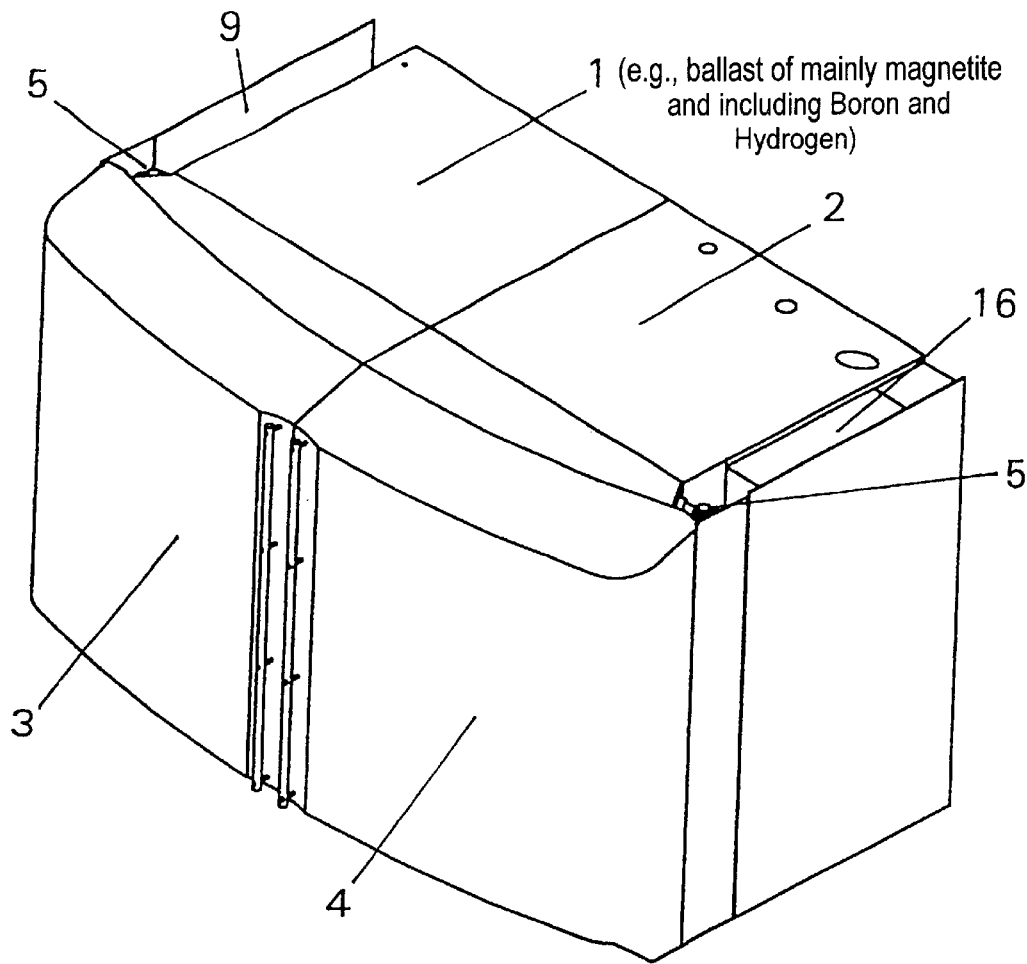
FIG. 1 is a three dimensional view of the apparatus hosting the system for PET isotope production.

An overall picture of the apparatus according to the present invention is disclosed in FIG. 1 and consists of four moulded sections, two fixed section 1 and 2 and two additional movable sections 3 and 4 forming doors. The installation of a PET isotope production system normally includes rigging work of a relatively heavy cyclotron device. Being able to, in a simple way, move, i.e. open, the additional radiation shield sections 3 and 4 constituting the doors provides an effective method to quickly access and service the PET isotope production system.

The match casting technology makes the fitting between the sections almost perfect, i.e. no slots, and close fitting to floor surface due to tight casting tolerances. The no time consuming alignment of shield sections is valuable when installing the PET isotope production system.

Figure 3:
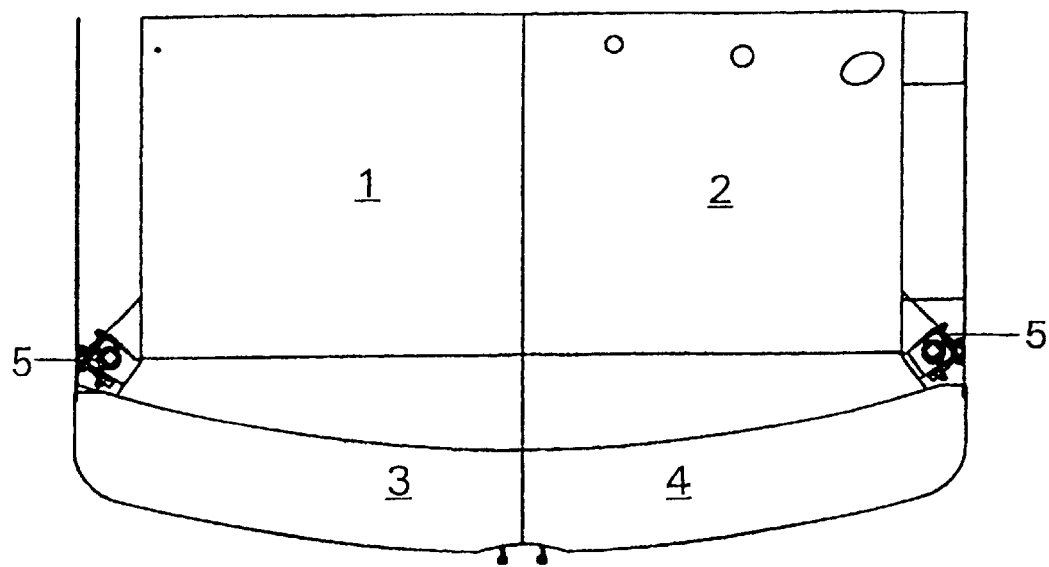
FIG. 3 is a top view of the apparatus and system according to FIG. 1.
Figure 4:
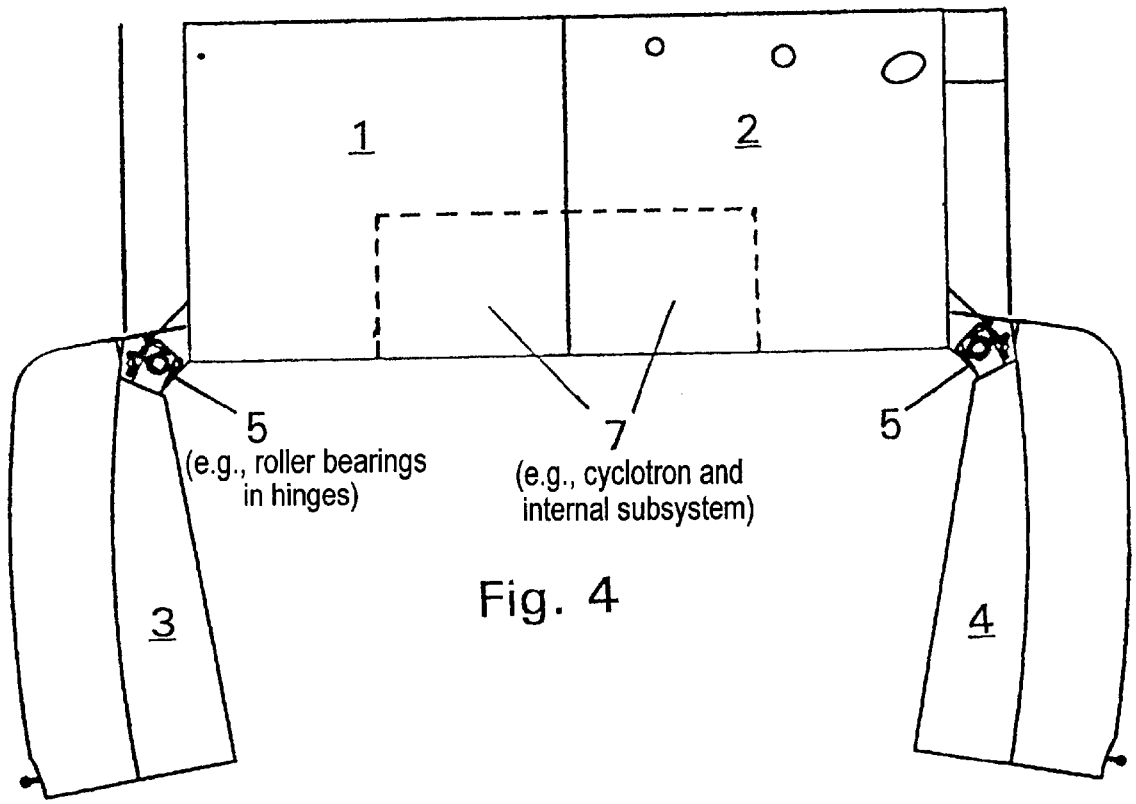
FIG. 4 is a view according to FIG. 3 showing the apparatus and the system with its radiation shielding doors opened for simple access of its internal cyclotron accelerator.

To achieve a simple opening of the radiation shield the sections 3 and 4, according to FIGS. 3 and 4, are forming doors on heavy-duty hinges taking up the load of the weight of the sections 3 and 4. Such a door section in a preferred embodiment has a weight of the order 7–8 tons, and thus the entire radiation shield has a mass corresponding to 10 m$^3$ of special concrete. Correspondingly each section 1 and 2 has a weight of 10–11 tons. A portion of each of the hinges 5 is fixedly moulded into the sections forming the concrete constituting the radiation shield, thereby eliminating all risks for having to perform adjustments over time (i.e. the hinges in fact forming an integral part of the shield)

Furthermore these doors 3, 4 are suspended on roller bearings in the hinges 5 forming a virtually "zero friction system" making door motion possible with a very low driving force which also is beneficial for eventual pinch hazards. Additionally the hinges 5 are adjustable in all directions facilitating all the options for the necessary final fine adjustment, to obtain a non-leakage radioactive and an almost airtight closure of the casing design enclosing the cyclotron device.

The casing according to the invention does not need any floor penetrations for installation of this "MINItrace" Integrated Radiation Shield. The user will be able to use an existing floor surface and there will be no time consuming preplanning and surface breaking needed for cable ducts, radiation shield rails and driving systems. Preferably before installation of the "MINItrace" Integrated Radiation Shield the floor surface may be treated with a self levelling low viscosity resin making the floor surface perfectly flat and levelled and ready to use after one night of hardening. On top of the section 2 there are situated a number of intake openings for the externally separated circuits, for instance for the wiring.

Each radiation shield section as well as the cyclotron device are equipped with lifting fittings for hydraulic jack rollers making lifting and movement of these heavy components quick and easy during the installation phase.

The "MINItrace" radiation shield consists of a dense concrete body especially designed to balance attenuation properties and the volume/weight ratio of the shield. The heavy ballast is chosen to be mainly iron ore for good gamma radiation attenuation with additional Boron and Hydrogen components to strengthen the neutron radiation attenuation capacity. In a preferred embodiment the radiation shield is having a hydrogen radiation protection mass of the order 25 kg/M$^3$ and 5–10 kg/M$^3$ of pure Boron and maximising the density by means of a magnetite (black ore $Fe_3O_4$) content for obtaining a final density of the order 3.5.

Furthermore, the targets are surrounded by a shielding of sandwich type containing PE plastics and lead (Pb). Finally the "MINItrace" radiation shield will form a virtually airtight container which prevents accidental leakage of radioactivity from the "MINItrace" interior system to the outside of the casing to create a low radiation environment in a room where the system is operating. Connections are easily provided for creating an under-pressure inside the shield (if regulations call for this). Also note that no air circulation from the surrounding air outside the shield is necessary for cooling purposes of the interior systems of the radiation shields, which assists in keeping the external environment of the casing at very low radiation hazard.

Figure 2:
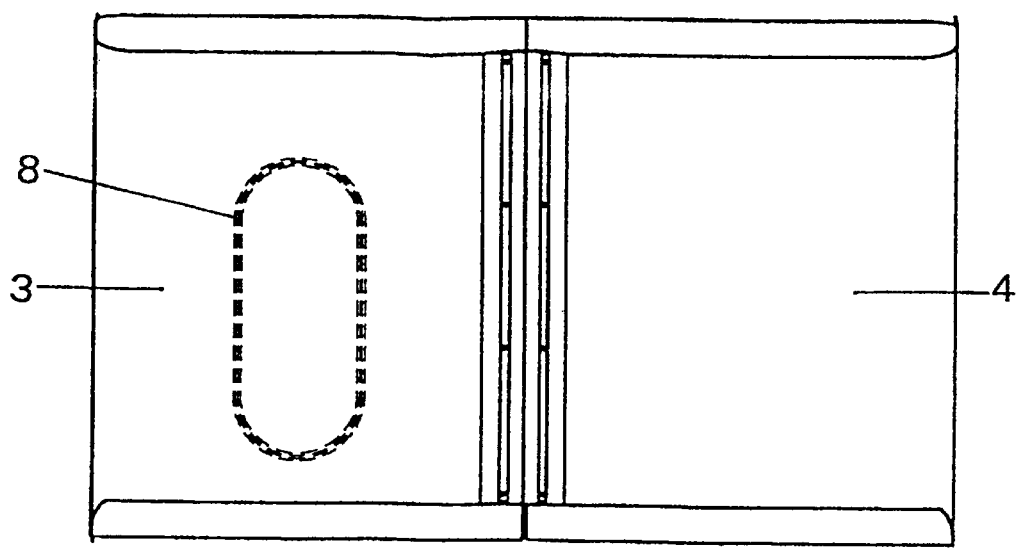
FIG. 2 is a front view of the apparatus and system according to FIG. 1.

Inside the radiation shield there is a space 7 housing a cyclotron with its internal subsystems like ion source, radio frequency electrode system and beam extraction elements and the visible subsystems such as vacuum case and pumps, targets with cooling water, and target window cooling. For easy maintenance of the cyclotron its magnet coils and poles are positioned such that the plane of the ion beam is vertical. Due to this design and the movable sections 3 and 4 the vacuum chamber of the cyclotron can even be divided in this vertical plane for simple access of its interior containing the closely spaced electromagnetic poles forming the acceleration gap for the ion beam and the other internal subsystems. This cyclotron is particularly designed for acceleration of a negative hydrogen ion beam then particularly used for production of short lived radioactive diagnostic tracers for medical applications. Also integrated in the radiation shield there is provided a Waste Gas Delay Line 8 positioned within the concrete portion 1, which is indicated in FIG. 2. It consists of a "long" plastic tube embedded in the concrete in such a way that the concrete will provide full radiation shielding for potential radioactivity loaded into the Waste Gas Delay Line 8.

Figure 5:
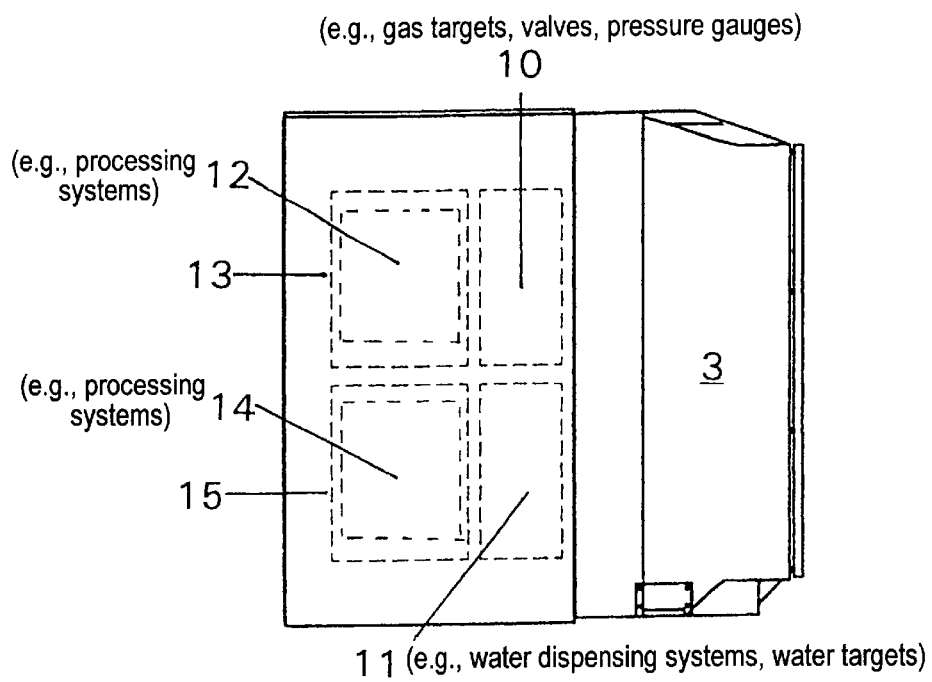
FIG. 5 is a left side view of the apparatus and system according to FIG. 1.
Figure 6:
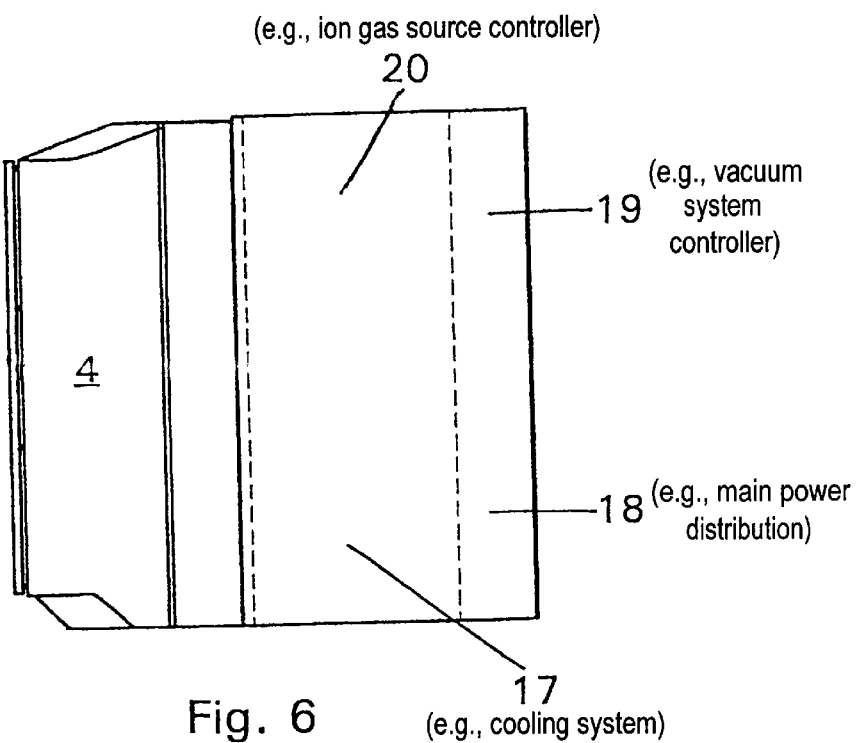
FIG. 6 is a right side view of the apparatus and system according to FIG. 1.

At the left side of the concrete casing portion 1 there is created a further compartment 9 (indicated in FIGS. 1 and 5). The compartment 9 offers target media handling 10 for the gas targets (e.g., isotopes $^{11}C$, and $^{15}O$) consisting of valves and pressure gauges and water dispensing systems 11 for the water targets (e.g., isotopes $^{13}N$, and $^{18}F$), the processing systems 12 for tracers $^{15}O$ and processing systems 14 for tracers $^{11}C$. The compartment 9 further contains a lead radiation shield 13 embracing the $^{15}O$ processing system 12 and a similar lead radiation shield 15 for the $^{11}C$ processing system 14. The lead shields 13, 15 are furnished with doors supported by hinges for easy access of the gas processing systems.

At the right shield side of the "MINItrace" casing there is also, still a compartment 16 (indicated in FIGS. 1 and 6) containing the secondary cooling system 17, mains power distribution 18, vacuum system controller 19 and the ion gas source controller 20.

Further at the top of the radiation shield created by the four portions 1–4 there are arranged shield surface driving motors for motions for doors as well as warning signs, e.g. indicating "Magnet field active", "Beam on".

Thus, the disclosed apparatus according to the present invention forms an integrated closed radiation-proof system for PET isotope production, which can easily be housed in connection to a main hospital for an easy access of short-lived radioactive tracers for medical diagnostic purposes.

The advantages of the present disclosed system primary lies in the design of the compact self-supporting radiation-proof casing which then easily can be applied as a localised facility.

What is claimed is:

1. An integrated shielded system for Positron Emission Tomography isotope production constituting a casing, comprising:
   a first compartment inside the casing containing a cyclotron device including standard subsystems;
   a second compartment including a plurality of sub-compartments comprising:
   a first sub-compartment for handling gas targets consisting of valve and pressure gauges;
   a second sub-compartment for water dispensing systems for water targets;
   a third sub-compartment including a first additional radiation shield and containing additional processing systems including valves, pressure and flow sensors, ovens and inside the first additional radiation shield; and
   a fourth sub-compartment including a second additional radiation shield containing additional processing systems and valves, pressure and flow sensors, and ovens inside the second additional radiation shield;
   a third compartment containing a secondary cooling system, a main power distribution, a vacuum system controller and an ion source gas control; and
   wherein the system constitutes a closed radiation-proof system by means of a casing consisting of four molded sections, wherein a first and a second section constitute a main body containing said first compartment and a third and a fourth section constitute a pair of closing doors for encompassing said first compartment into a sealed radiation shield, whereby said first section additionally contains a Waste Gas Delay Line embedded in shielding material of the first section.

2. The system according to claim 1, wherein the four sections consist of a dense concrete designed to balance attenuation properties and a volume/weight ratio of the shield, and further comprising a ballast formed mainly of magnetite for high gamma attenuation and containing additional Boron and Hydrogen components to strengthen a neutron attenuation capacity.

3. The system according to claim 2, wherein the Waste Gas Delay Line consists of a plastic tube formed into a coil to obtain a proper gas delay and embedded into the concrete material of the first section of the casing.

4. The system according to claim 2, wherein the third and fourth section constituting a pair of closing doors are suspended on roller bearings in hinges, whereby a portion of each hinge is fixedly molded into the concrete forming the first and third sections or second and fourth sections, respectively.

5. The system according to claim 1, wherein the first and second additional radiation shields are formed by a sandwich type shielding containing plastics and lead.

6. An apparatus constituting an integrated Positron Emission Tomography isotope production system comprising:
    a first compartment containing a cyclotron device including vacuum pumping systems, targets, target support systems, cooling water systems and target window cooling systems;
    a second compartment including a plurality of sub-compartments comprising:
        a first sub-compartment for handling gas targets consisting of valve and pressure gauges;
        a second sub-compartment for water dispensing systems or water targets;
        a third sub-compartment including a first additional radiation shield and containing additional processing systems including valves, pressure and flow sensors, and ovens inside the first additional radiation shield; and
        a fourth sub-compartment including a second additional radiation shield containing additional processing systems and valves, pressure and flow sensors, and ovens inside the second additional radiation shield;
    a third compartment containing a secondary cooling system, a main power distribution, a vacuum system controller and an ion source gas control; and
    wherein the system constitutes a closed radiation-proof system by means of a casing consisting of four molded sections, whereby a first and a second section constitute a main body containing said first compartment and a third and a fourth section constitute a pair of closing doors for encompassing said first compartment into a sealed radiation shield, whereby said first section additionally contains a Waste Gas Delay Line embedded in shielding material of the first section.

7. The apparatus according to claim 6, wherein the four sections consist of a concrete designed to balance attenuation properties and a volume/weight ratio of the shield and further comprising a ballast formed mainly of magnetite for high gamma attenuation and containing additional Boron and Hydrogen components to strengthen the neutron attenuation capacity.

8. The apparatus according to claim 7, wherein the Waste Gas Delay Line consists of a plastic tube formed into a coil to obtain a proper gas delay and embedded into the concrete material of the first section of the casing.

9. The apparatus according to claim 7, wherein the third and fourth section constituting a pair of closing doors are suspended on roller bearings in hinges, whereby a portion of each hinge is fixedly molded into the concrete forming the first and third sections or second and fourth sections, respectively.

10. The apparatus according to claim 6, wherein said first and second additional radiation shields are formed by a sandwich type shielding containing plastics and lead.

* * * * *